(12) United States Patent
Wada et al.

(10) Patent No.: US 6,583,197 B1
(45) Date of Patent: Jun. 24, 2003

(54) DENTAL ADHESIVE COMPOSITION

(75) Inventors: Tohru Wada, Takatsuki (JP); Kunio Ikemura, Joyo (JP); Yoshiaki Kouro, Hirakata (JP); Katsuya Kimoto, Ibaraki (JP); Kazuya Shinno, Uji (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 09/609,696

(22) Filed: Jul. 6, 2000

(30) Foreign Application Priority Data

Jul. 8, 1999  (JP) ............................................. 11-194450
Jun. 16, 2000 (JP) ......................................... 2000-181729

(51) Int. Cl.$^7$ ................................................. C08F 2/46
(52) U.S. Cl. ............................ 522/84; 522/81; 522/79; 522/83; 522/85; 522/182; 522/908; 523/118; 523/122
(58) Field of Search ............................ 522/903, 84, 85, 522/86, 908, 182, 77, 79, 81, 83; 523/118, 113, 122, 114, 116

(56) References Cited

U.S. PATENT DOCUMENTS

| | | | |
|---|---|---|---|
| 4,732,943 A | * 3/1988 | Beech et al. ................. 525/303 |
| 4,872,936 A | * 10/1989 | Engelbrecht ............. 156/307.3 |
| 5,063,257 A | * 11/1991 | Akahane et al. ............. 523/116 |
| 5,130,347 A | * 7/1992 | Mitra ......................... 522/149 |
| 5,171,763 A | 12/1992 | Ohno et al. | |
| 5,367,002 A | * 11/1994 | Huang et al. ................ 523/115 |
| 5,374,664 A | 12/1994 | Zalsman et al. | |
| 5,883,153 A | * 3/1999 | Roberts et al. ............. 501/151 |

FOREIGN PATENT DOCUMENTS

| | | |
|---|---|---|
| EP | 0705590 | 4/1996 |
| JP | 62149715 | 7/1987 |
| JP | 26358 | 1/1990 |
| JP | 5255033 | 10/1993 |
| JP | 627047 | 4/1994 |
| JP | 826925 | 1/1996 |
| JP | 8500080 | 1/1996 |
| JP | 830717 | 2/1996 |
| JP | 2634276 | 4/1997 |
| JP | 10236912 | 9/1998 |
| WO | 9423687 | * 10/1994 |

OTHER PUBLICATIONS

Database WPI, Section Ch, Week 199846, Derwent Publications Ltd.
Patent Abstracts of Japan, vol. 016, No. 106, Mar. 16, 1992.
Search Report dated Aug. 16, 2002.

* cited by examiner

*Primary Examiner*—James J. Seidleck
*Assistant Examiner*—Sanza L. McClendon
(74) *Attorney, Agent, or Firm*—Stevens, Davis, Miller & Mosher, L.L.P.

(57) ABSTRACT

A dental adhesive composition comprising:

(A) 100 parts by weight of a polymerizable unsaturated monomer containing 5% by weight or more of a radical polymerizable monomer having an acid group;

(B) 35 to 100 parts by weight of an acid-reactive filler;

(C) 35 to 100 parts by weight of water;

(D) 5 to 100 parts by weight of a water-soluble organic solvent; and, (E) 0.1 to 10 parts by weight of a polymerization catalyst.

27 Claims, 2 Drawing Sheets

Immersing period in ion-exchanged water (weeks)

DENTAL ADHESIVE COMPOSITION

BACKGROUND OF THE INVENTION

1. Field of the Invention

The present invention relates to a one-step dental adhesive composition with which a sustained release of fluorine can be effected. More particularly, a composition of the invention, when employed to make a bond between a dental restorative material such as a composite resin or a compomer and a substrate such as a biological hard tissue, especially an enamel or a dentin of a natural tooth as well as a glass ionomer cement, can be formed adhesive layer between them even in a convenient single step to give a firm adhesion, and, at the same time, exhibits an excellent sustained release of fluorine and an excellent material stability experience as a reduced water absorption, a reduced swelling and a reduced dimensional change. Accordingly, the present invention relates to a dental adhesive composition which can be handled conveniently by a one-step operation, exhibits an excellent durability, gives a high level of a sustained fluorine release, and thus is expected to give a secondary caries suppression.

2. Description of the Prior Art

In the field of a dentistry, an adhesive restoration method using a composite resin is brought into an increasing use in response to a recent advancement in a dental bonding technology. One such adhesive restoration method employed generally is a clinical procedure in which the surface of a tooth is treated with an etching agent containing an acid such as phosphoric acid and then subjected to an adhesive priming followed by a treatment with an adhesive composition containing a radical-polymerizable monomer having an acid group. However, this method involves a problematically complicated 3-step operation, and it gives an insufficient adhesion to a dentin although it gives a satisfactory adhesion to an enamel. More recently, a 2-step system employing a treatment with a so-called self etching primer and an adhesive composition was proposed. This method is brought into a clinical use increasingly due to its relatively easy handling and a high adhesiveness to a dentin. For example, JP 2634276 discloses a 2-step treatment in which a ground dentin is treated with a primer composition containing water, a polymerizable compound having a hydroxyl group, a polymerizable compound having an acid group and a curing agent and then with a photopolymerizable bonding agent whereby imparting an enamel and the dentin with a high adhesiveness. Nevertheless, a dental adhesive exerting a higher ability of binding to a substrate such as an enamel or a dentin more conveniently by an easier one-step procedure is still demanded strongly at a clinical stage of the dental surgery. Furthermore, a dental adhesive capable of providing not only a strong tooth adhesion but also a sustained release of fluorine which leads to inhibit the formation of a secondary caries is desired to be developed.

On the other hand, a glass ionomer (glass polyalkenoate) cement is considered increasingly to be of a clinical value since it exhibits a sustained release of fluorine and a satisfactory dental adhesion. Such glass ionomer cement undergoes a setting due to the formation of a hydrogel salt as a result of an acid-base reaction between a basic calcium aluminofluorosilicate glass and an acidic polymeric electrolite which is a homopolymer or a copolymer of an unsaturated carboxylic acid. A cement of this type is useful especially as a dental cement since it has an excellent biocompatibility and can adhere to a teeth where it can release a fluorine ion. However, it involves a problem relating to the material characteristics which are experienced as a slow setting between a glass and an ionomer as well as a brittleness of a hardened body whose matrix is in a gel structure.

Recently, a so-called photocuring glass ionomer cement was proposed. Mostly, it comprises a polyalkenoic acid, a reactive glass and a photopolymerizable monomer, and its photocuring allows the time period for achieving a desired hardness of the cement to be reduced when compared with a conventional glass ionomer cement, as described, for example, in JP-A-62-149715, JP-A-5-255033, JP-W-8-500080, JP-A-2-6358, JP-B-6-27047, JP-A-8-26925 and JP-A-8-30717. Nevertheless, none of these disclosed methods can achieve an actually strong adhesion to a substrate such as an enamel or a dentin.

JP-B-6-89050 discloses a setting composition (compomer) consisting of a vinyl monomer having an acid group, an ion-releasing filler and a polymerization initiator, especially a setting composition which requires no bonding agent for the adhesion, ensures a firm adhesion to a tooth even when being set as wet, and provides a hardened body having a sufficient hardness. However, since this composition exhibits an instability against water when used as a single pack, and also exhibits a poor storage stability, thus posing a problem when employed practically. When used as being divided into two components, a hardened article has problematically high water absorption and swelling. JP-A-10-236912 also discloses a adhesive composition comprising 100 parts by weight of a polymerizable unsaturated monomer containing 5% by weight or more of a polymerizable unsaturated monomer having an acid group, 2 to 30 parts by weight of a polyvalent metal ion-releasing filler, 3 to 30 parts by weight of water and 0.01 to 10 parts by weight of a polymerization initiator which is purported to be handled conveniently without requiring any pre-treatment and to give a strong adhesion to both of an enamel and a dentin but shows a reduced adhesion strength when the amount of water exceeds 30 parts by weight. However, this composition exhibits an extremely low sustained fluorine release from a cured adhesive, and has a problematically poor adhesive durability because of its high water absorption and swelling.

SUMMARY OF THE INVENTION

Accordingly, an objective of the present invention is to provide a dental adhesive composition which can adhere, by a convenient one-step operation, firmly to a biological hard tissue, especially an enamel or a dentin of a natural tooth as well as a glass ionomer cement, which exhibits an excellent sustained release of fluorine which may serve to inhibit the formation of a secondary caries, and which are excellent also in the material stability and in the adhesive durability due to its less oral water absorption and swelling.

Thus, the present invention relates to a dental adhesive composition comprising (A) 100 parts by weight of a polymerizable unsaturated monomer containing 5% by weight or more of a radical polymerizable monomer having an acid group, (B) 35 to 100 parts by weight of an acid-reactive filler, (C) 35 to 100 parts by weight of water, (D) 5 to 100 parts by weight of a water-soluble organic solvent; and (E) 0.1 to 10 parts by weight of a polymerization catalyst.

The present inventors made an effort to solve the problems described above which are associated with a dental adhesive and to obtain a dental adhesive capable of exerting a strong adhesion with a simple handling, and finally discovered that the adhesive composition of the present invention can adhere, by a convenient one-step operation, firmly to a substrate such as a biological hard tissue, especially an enamel or a dentin of a natural tooth, exhibits an excellent sustained release of fluorine which may serve to inhibit the formation of a secondary caries, and are excellent also in the material stability and in the adhesive durability due to its less oral water absorption or dimensional change, thus establishing the present invention.

In the invention, "a dental adhesive" means a material relating to an adhesive restoration employed clinically in a dental surgery, such as a dental bonding agent, a dental adhesive resin cement, a dental fissure sealant, a dental orthodontic bracket adhesive, a temporary sealing material (temporary sealing adhesive) and a root canal filling material and the like.

BRIEF DESCRIPTION OF THE DRAWINGS

In FIG. 1, the number 1 means full enamel margin cavity (φ4.0 mm), the number 2 means saucer shaped cervical cavity (φ4.0 mm), and the number 3 means dental pulp.

DETAILED DESCRIPTION OF THE INVENTION

Figure 1:
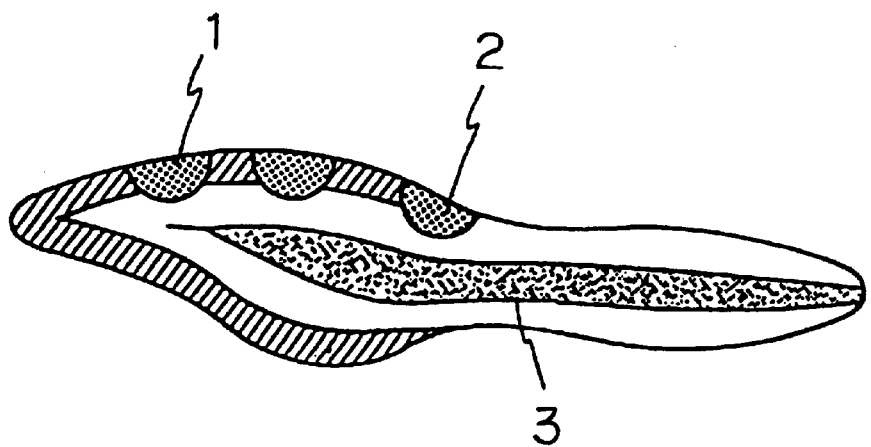
FIG. 1 shows a sectional view of a cavity for a marginal leakage test, which was formed on a bovine anterior tooth.

A radical polymerizable monomer having an acid group is employed in an amount of at least 5% by weight of a polymerizable unsaturated monomer constituting the adhesive composition of the present invention. A radical polymerizable monomer having an acid group employed in the present invention is a radical polymerizable monomer having a functional group capable of reacting with an acid-reactive filler, and a particularly preferred acid group is a carboxyl group, an acid anhydride residue and a phosphate group. Examples of the radical polymerizable monomers having such acid groups are 4-(meth)acryloxyethyl- trimellitic acid [this abbreviation stands for 4-acryloxyethyltrimellitic acid and 4-methacryloxyethyltrimellitic acid, and is applied analogously to the following description], 4-(meth)acryloxyethyltrimellitate anhydride, 11-(meth)acryloxy-,11-undecane dicarboxylic acid, 2-(meth)acryloxyethylphosphate, bis[2-(meth)acryloxyethyl]phosphate, 2-(meth)acryloxyethyl phenyl hydrogen phosphate, 10-(meth)acryloxydecyl dihydrogen phosphate, vinylphosphonic acid, p-vinylbenzylphosphonic acid, (2-(meth)acryloxy)ethyl-3-phosphonopropionate, (6-(meth)acryloxy)hexyl-3-phosphonopropionate, (6-(meth)acryloxy)hexyl-phosphonoacetate, 10-(meth)acryloxy)decyl-3-phosphonopropionate, amino acid N-(meth)acrylate derivatives such as N-(meth)acryloylaniline, N-(meth)acryloyltyrosine, N-(meth)acryloylaspartic acid, N-phenylglycidyl(meth)acrylate, N-tolylglycine glycidyl (meth)acrylate, p-vinylbenzoic acid, aromatic aminocarboxylic acid N-(meth)acrylate derivatives such as N-(meth) acryloylaminobenzoic acid, N-(meth)acryloylaminosalicylic acid, acid salts such as sodium salts of (meth) acrylic acid, itaconic acid, maleic acid and N-phenylglycine glycidyl (meth)acrylate, sodium salt of N-tolylglycine glycidyl (meth)acrylate, and the like. 4-(meth) acryloxyethyltrimellitic acid, 4-(meth)acryloxyethyltrimellitate anhydride, (6-(meth)acryloxy)hexyl-3-phosphonopropionate and (6-(meth)acryloxy)hexyl-3-phosphonoacetate are particularly preferred. Only one of or a combination of two or more of the compounds listed as a radical polymerizable monomer containing an acid group may be employed.

Such radical polymerizable monomer containing an acid group exemplified above reacts with an acid-reactive filler, especially with an acid-reactive glass in the presence of water. Accordingly, when such acid-reactive glass is combined with a radical polymerizable monomer containing an acid group, the constituents of an adhesive composition is used preferably in the state where they are divided into two or more.

A radical polymerizable monomer containing an acid group is used in an amount of at least 5% by weight, preferably 15% by weight, more preferably 25% by weight of the polymerizable unsaturated monomer constituting a dental adhesive composition. An amount of less than 5% by weight results in a reduction in the adhesiveness and in the level of a sustained fluoride release and an increase in the water absorption and in the swelling.

An acid-reactive filler which can be employed in the present invention is a metal oxide, a metal salt, hydroxyapatite or an acid-reactive glass and the like, which are contained in silicate cements, zinc phosphate cements, zinc-carboxylate cements and glass ionomer cements which are employed conventionally in the field of a dental surgery. An acid-reactive glass is particularly preferred. A preferred acid-reactive glass is an acid-reactive glass used in a glass ionomer cement, with a fluoroaluminosilicate glass being preferred particularly.

A fluoroaluminosilicate glass can be produced by a known glass production method. For example, it can be produced from a starting material for a glass, selected from silica, alumina, aluminum hydroxide, aluminum silicate, mullite, calcium silicate, strontium silicate, sodium silicate, sodium carbonate, calcium fluoride, aluminum fluoride, strontium fluoride, aluminum phosphate, sodium phosphate and the like, by fusing at a high temperature of 1000° C. or higher followed by cooling and grinding. A preferred composition of a fluoroaluminosilicate glass employed in the present invention is shown below.

| | |
|---|---|
| Calcium oxide (CaO) | 5 to 40% by mole |
| Silica (SiO$_2$) | 15 to 70% by mole |
| Alumina (Al$_2$O$_3$) | 10 to 50% by mole |
| Sodium oxide (Na$_2$O) | 0 to 7% by mole |
| Phosphorus pentoxide (P$_2$O$_5$) | 0 to 7% by mole |

The fluorine level of this glass is preferably 5 to 60% by mole. While calcium oxide is employed in the composition shown above, any alkaline earth metal oxide may also be employed. At least a part of an alkaline earth metal may be replaced with a lanthanide metal such as lanthanum, gadolinium and ytterbium. A part or all of the alumina in the glass may also be replaced with a metal in Group III other than aluminum. Similarly, a part of the silica in the glass may also be replaced with zirconium oxide or titanium oxide. When a glass contains strontium, lanthanum, gadolinium, ytterbium or zirconium, then the glass is X-ray opaque.

While a fluoride-containing glass employed in the present invention may be produced by any known method, it is produced preferably by a fusing method and a sol-gel method. In such method, for example, a first solution containing a soluble aluminum compound and a soluble silicon compound is reacted with a second solution containing a soluble compound of a metal in Group II to form a gel, which is recovered by drying in an oven or by lyophilization. In this method, an additive employed ordinarily in the production of a glass, such as a flux agent, is not required and a relatively lower temperature can be used. Accordingly, a glass having a higher transparency than that of a conventional glass can be obtained.

Another compound, such as an organic metal or an inorganic salt in an alcohol solution may be added to a sol to obtain a divalent or trivalent glass.

In order to accelerate a gelation process, an acidic or basic solvent may be added to this sol-gel reaction mixture. In such case, a homogeneous refractory glass can be obtained at a relatively lower temperature.

This sol-gel method is suitable especially for the production of a gadolinium-containing glass and the following 5-components glass.

$$X_nO_m\text{—}CaO\text{—}Al_2O_3\text{—}SiO_2\text{—}F$$

wherein $X_nO_m$ is an oxide of an X-ray opaque substance.

While such 5-components glass is difficult to produce, it can readily be produced by a sol-gel method. Aluminum sec-butoxide (Asb) in isobutyl alcohol and ethanol as a CaO source, tetraethyl silicate as an $SiO_2$ source, a 40% hydrofluoric acid as a F source, an ethanol-soluble $Gd(NO_3)_3$ or a solution in methanol as a $Gd_2O_3$ source may also be employed substitutionally.

Calcium oxide may also be replaced with an anhydrous $Ca(NO_3)_2$ dissolved in ethanol at 50° C. Such solution is admixed at 50° C. with stirring. Thereafter, it may be refluxed at 70° C. After drying, the material is ground while still soft, and then dried at a temperature of 400 to 500° C. Then it may further be pulverized to a desired size. A fluoroaluminosilicate glass employed in this invention may also be one obtained by a conventional fusing method.

The amount of a fluoroaluminosilicate glass as an acid-reactive filler in a dental adhesive composition according to the present invention is 35 to 100 parts by weight, preferably 35 to 80 parts by weight per 100 parts by weight of a polymerizable unsaturated monomer containing 5% by weight or more of a radical polymerizable monomer having an acid group as Component (A). An amount less than 35 parts by weight or exceeding 100 parts by weight leads to a reduction in the adhesion and in the level of a sustained fluoride release and an increase in the water absorption and the swelling.

An acid-reactive filler employed in the present invention has a mean particle size of 0.1 to 10 μm, preferably 0.5 to 5 μm.

A water employed in this invention is preferably one which has clinically acceptable storage stability and pharmaceutical components and which does not contain any impurity by which the components of the composition and the adhesive ability are affected adversely, and a distilled water (or a purified water) or an ion exchange water (or a deionized water) is employed preferably.

The amount of a water to be added in this invention is 35 to 100 parts by weight, preferably 35 to 80 parts by weight per 100 parts by weight of a polymerizable unsaturated monomer containing 5% by weight or more of a radical polymerizable monomer having an acid group. An amount less than 35 parts by weight or exceeding 100 parts by weight leads to a reduction in the adhesiveness and in the level of a sustained fluoride release and an increase in the water absorption and the swelling.

JP-A-10-236912 also discloses a adhesive composition comprising 100 parts by weight of a polymerizable unsaturated monomer containing 5% by weight or more of a polymerizable unsaturated monomer having an acid group, 2 to 30 parts by weight of a polyvalent metal ion-releasing filler, 3 to 30 parts by weight of water and 0.01 to 10 parts by weight of a polymerization initiator which is purported to be handled conveniently without requiring any pre-treatment and to give a strong adhesion to both of an enamel and a dentin but shows a reduced adhesive strength when the amount of water exceeds 30 parts by weight. However, this composition exhibits an extremely low sustained fluoride release from a cured adhesive, and has a problematically poor adhesive durability because of its high water absorption (168.0 to 285.5 μg/mm$^3$) and swelling (2.32 to 6.24%). It was revealed in the extensive study by the present inventor that the increase in the amounts of water and an acid-reactive filler per 100 parts by weight of a polymerizable unsaturated monomer containing 5% by weight or more of a radical polymerizable monomer having an acid group to 35 to 100 parts by weight and 35 to 100 parts by weight, respectively, and an additional incorporation of 5 to 100 parts by weight of a water-soluble organic solvent rather resulted in an improved adhesion to a tooth. More surprisingly, it was also revealed that the water absorption was reduced to the range from 10 to 90 μg/mm$^3$, that the dimensional change of a cured adhesive due to the swelling was reduced, and that the level of a sustained fluoride release was increased. In addition, the durability of the adhesion to a tooth and the marginal sealing performance were also revealed to be improved.

A water-soluble organic solvent employed in the present invention serves to improve the solubility of a radical polymerizable monomer having an acid group in water whereby yielding a homogenous solution and to improve the adhesion performance. Examples of such water-soluble organic solvent are alcohol compounds such as methyl alcohol, ethyl alcohol, 1-propanol, isopropyl alcohol, 2-methyl-1-propanol, 2-methyl-2-butanol, 2-propen-1-ol, 1,3-butanediol, 1,4-butanediol, 1,2,6-hexanetriol, trimethylol propane, diethylene glycol, triethylene glycol, tetraethylene glycol, propylene glycol, 2-methoxyethanol, 2-ethoxyethanol, 2-(methoxyethoxy)ethanol, 2-(ethoxyethoxy)ethanol, 2-(ethoxyethoxy)ethanol and the like as well as ketone compounds such as acetone, methylethylketone and the like. Among these substances, acetone, ethyl alcohol and isopropyl alcohol are employed preferably. A mixture of two or more of the water-soluble organic solvents listed above may also be employed.

The amount of such water-soluble organic solvent to be added is 5 to 100 parts by weight, preferably 10 to 50 parts by weight per 100 parts by weight of a polymerizable unsaturated monomer containing 5% by weight or more of a radical polymerizable monomer having an acid group. An amount less than 5 parts by weight results in an insufficient solvent ability of dispersing a polymerizable unsaturated monomer in water, while an amount exceeding 100 parts by weight results in a reduced adhesion to an enamel or a dentin.

In the present invention, a radical polymerizable monomer other than a radical polymerizable monomer having an acid group may be incorporated as a polymerizable unsaturated monomer, and such radical polymerizable monomer having no acid group is useful since it serves to improve the cohesive force of the layer of a one-step adhesive whereby imparting a higher adhesiveness. Such radical polymerizable monomer is every radical polymerizable monomer having no acid group, such as, for example, (meth)acrylate ester derivatives, alkylene glycol di(meth)acrylates, alkyl di(meth)acrylates, epoxy di(meth)acrylates, bisphenol A-alkyl di(meth)acylates, urethane di(meth)acrylates, urethane tri(meth)acrylates, urethane tetra(meth)acrylates, hydroxylalkyl (meth)acrylates, Si group-carrying (meth) acrylates, SH group- or —S—S—group-carrying (meth) acrylates and styrene derivatives. Typically, methyl(meth) acrylate, ethyl(meth)acrylate, ethylene glycol di(meth) acrylate, triethylene glycol di(meth)acrylate, hexamethylene glycol di(meth)acrylate, 1,6-hexane di(meth)acrylate, bisphenol A-diglycidyl (meth)acrylate, di(meth) acryloxyethyl-2,2,4-trimethylhexamethylene diurethane, di(meth)acryloxyisophorone diurethane, 2-hydroxyethyl (meth)acrylate, 6-hydroxyhexyl(meth)acrylate, 2-hydroxypropyl(meth)acrylate, glycerol di(meth)acrylate, styrene, urethane acrylates, alkylene glycol dimethacrylates, γ-methacryloxypropyltrimethoxysilane and the like. The monomers preferred are ethylene glycol di(meth)acrylate, triethylene glycol di(meth)acrylate, hexamethylene glycol di(meth)acrylate, 1,6-hexane di(meth)acrylate, bisphenol A-diglycidyl (meth)acrylate, di(meth)acryloxyethyl-2,2,4-trimethylhexamethylene diurethane, di(meth) acryloxyisophorone diurethane, 1,1,1-tri{6-[(1-acryloxy-3-phenoxy)-2-isopropoxycarbonylamino]-hexylcarbamoyloxymethyl}propane, 2-hydroxyethyl(meth)acrylate, 2-hydroxypropyl(meth)acrylate, glycerol di(meth)acrylate and the like. Among them 2-hydroxyethyl(meth)acrylate, bisphenol A-diglycidyl(meth)acrylate, urethane acylates, alkylene glycol dimethacrylates are preferred particularly. Any of these monomers may be used as far as it is compatible with water and a monomer having acid group. Only one or a mixture of two or more of the monomers listed above may be employed.

While a polymerization catalyst used in the invention may be any known polymerization catalyst, those particularly specified are a radical polymerization initiator and promoter for a redox polymerization and a photopolymerization, such as barbituric acid derivatives, organic peroxides, α-diketones, amines, sulfinic acids, organotin compounds and the like. Only one or a mixture of two or more of the substances listed above may be employed.

A barbituric acid derivative is a compound represented by Formula:

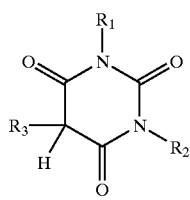

wherein $R_1$, $R_2$ and $R_3$ are same or different, and each represents an aliphatic, aromatic, alicyclic or heterocyclic residue optionally substituted with a halogen atom, an alkyl group, an alkoxy group, an allyl group and a cyclohexyl group or a hydrogen. Typically, barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethylbarbituric acid, 1,3-dimethyl-5-cyclopenthylbarbituric acid, 1,3-dimethyl-5-cyclohexylbarbituric acid, 1,3-dimethyl-5-phenylbarbituric acid, 1-cyclohexyl-5-ethylbarbituric acid, 1-benzyl-5-phenylbarbituric acid and thiobarbituric acids as well as salts thereof (preferably alkaline metal salts and alkaline earth metal salts), for example, sodium 5-butylbarbiturate, sodium 1,3,5-trimethylbarbiturate and sodium 1-cyclohexyl-5-ethylbarbiturate.

An organic peroxide may for example be benzoyl peroxide, 2,4-dichlorobenzoyl peroxide, t-butyl hydroperoxide, succinic acid peroxide, t-butyl peroxymaleic acid, t-butylperoxyisobutyrate and t-butyl perbenzoate.

A photopolymerization catalyst may be a photopolymerization initiator for a UV light and a visible light, such as benzoin alkylethers, thioxanthones and α-diketones including benzoin methylether, benzoin isopropylether, thioxanthone, 2-chlorothioxanthone, 2-hydroxy-3-(3,4-dimethyl-9H-thioxanthen-2-yloxy) N,N,N-trimethyl-1-propanaminium chloride, dibenzyl, camphorquinone and the like.

An amine is an aliphatic and aromatic, primary, secondary and tertiary amine, such as ethanolamine, triethylamine, dimethyl-p-toluidine, N,N-di(hydroxyethyl)-p-toluidine, N-phenylglycine, N,N-dimethylaminoethyl (meth)acrylate, N,N-diethylaminoethyl (meth)acrylate and the like. When these amines are used in combination with organic peroxides and sulfinic acids, they should be provided as being divided into two or more and mixed just before use since they are reactive with each other.

A sulfinic acid may for example be a sulfinic acid, an alkaline metal sulfinate and a sulfinylamide such as, for example, benzene sulfinic acid, p-toluenesulfinic acid, dodecylbenzene sulfinic acid, sodium benzenesulfinate, sodium p-toluenesulfinate, sodium dodecylbenzenesulfinate, benzensulfinylamide, N,N-dimethyl-p-toluene sulfinylamide, benzenesulfinylmorpholide, p-toluenesulfinylmorpholide and the like. When any of these metal sulfinates is used in combination with a radical polymerizable monomer having an acid group, the metal sulfinate and the radical polymerizable monomer having an acid group should be provided separately instead of being mixed and subsequently mixed just before use or one should be applied to the surface of a tooth and the other should then be applied thereon, whereby embodying the present invention, since they are reactive with each other.

An organotin compound is di-n-butyltin dimalate, di-n-octyltin dimalate, di-n-octyltin dilaurate, di-n-butyltin dilaurate, as well as a mixture thereof.

Other polymerization catalysts may for example be ascorbic acid, tributylborane and the like.

Any of the polymerization catalysts listed above may be used alone, or two or more of barbituric acid derivatives, organic peroxides, (α-diketones, amines, sulfinic acids and organotin compounds listed above may be employed in combination.

A polymerization catalyst employed in the present invention is preferably 1-benzyl-5-phenylbarbituric acid, 1-cyclohexyl-5-ethylbarbituric acid, 5-butylbarbituric acid, 1,3,5-trimethylbarbituric acid, benzoyl peroxide, t-butylperoxymaleic acid, succinic acid peroxide, camphorquinone, sodium benzensulfinate, sodium p-toluenesulfinate, di-n-butyltin malate, di-n-octyltin malate, di-n-octyltin laurate, di-n-butyltin dilaurate, or a mixture thereof.

The amount of a polymerization catalyst employed in the present invention is 0.1 to 10 parts by weight, preferably 0.5 to 7 parts by weight per 100 parts by weight of a polymerizable unsaturated monomer containing 5% by weight or more of a radical polymerizable monomer having an acid group. An amount less than 0.1 parts by weight or exceeding 10 parts by weight leads to a reduction in the adhesiveness.

To an adhesive composition of the present invention, an acid other than a radical polymerizable monomer having an acid group may also be added if necessary in an amount which affects the adhesive characteristics of the invention adversely. Such acid may for example be a monocarboxylic acid, a dicarboxylic acid, a tricarboxylic acid and a tetracarboxylic acid. A monocarboxylic acid may for example be formic acid, lactic acid, pyruvic acid, glycolic acid, chloroacetic acid, dichloroacetic acid, trichloroacetic acid, cyanoacetic acid and the like. A dicarboxylic acid may for example be tartaric acid, succinic acid, glutaric acid, maleic acid, malonic acid, citraconic acid, (o,m,p)-phthalic acid and the like. A tricarboxylic acid may for example be citric acid, tricarballyl acid, 1,3,5-pentanetricarboxylic acid, trimellitic acid and the like. Acid anhydrides of those listed above are also included.

In addition to an acid-reactive filler, a filler other than an acid-reactive filler may also be added in an amount by which the adhesive characteristics of the invention are affected adversely. While such filler itself is non-reactive with to a radical polymerizable monomer having an acid group, it may serve for various purposes, such as an increase in the mechanical strength of a cured adhesive, an X-ray opaque or a masking effect. Such filler may for example be silica, a fused silica, a quartz glass, alumina, aluminosilicate, a colloidal silica, barium sulfate, titanium oxide, an organic filler, or a preformed glass ionomer filler produced by subjecting a fluoroaluminosilicate glass, polyacrylic acid and water to an acid-base reaction followed by drying a resultant gel as disclosed in U.S. Pat. No. 5,883,153.

In an adhesive composition of the present invention, various additives such as an antioxidant, a surfactant and a thickening agent, in addition to the components discussed above, may also be added if necessary. An antioxidant may for example be hydroquinone, hydroquinone monomethylether, butylated hydroxytoluene and the like.

A surfactant may appropriately be added for improving a compatibility of a fluid. For this purpose, those surfactants which may be exemplified are sorbitan fatty acid esters, glycerin fatty acid esters, decaglycerin fatty acid esters, diglycein fatty acid esters, tetraglycerin fatty acid esters, hexaglycerin fatty acid esters, propylene glycol fatty acid esters, pentaerythritol fatty acid esters, polyoxyethylene sorbitan fatty acid esters, polyoxyethylene sorbit fatty acid esters, polyethylene polyoxypropylene alkylethers, polyoxyethylene alkylphenylethers, polyoxyethylene castor oils, polyoxyethylene hardened castor oils, polyoxyethylene lanolines, polyoxyethylene lanoline alcohols, polyoxyethylene beeswax derivatives, polyoxyethylene alkylamines, polyoxyethylene fatty acid amides, polyoxyethlene alkylphenyl formaldehyde condensates, alkyl sulfates, lecithin, polyoxyethylene alkylether acetates, alkylether carboxylic acids, alkylphosphates, polyoxyethylene alkylether phosphates, aliphatic amines, benzalkonium chloride and the like.

A thickening agent such as a colloidal silica, polyethylene glycol, glycerin, polyvinyl alcohol, methyl cellulose or carboxymethyl cellulose may also be added in order to obtain a suitable viscosity or to prevent the sedimentation of an acid-reactive filler.

When a radical polymerizable monomer having an acid group is provided separately from water in one embodiment of a dental adhesive of the present invention, the radical polymerizable monomer and an acid-reactive glass may be provided separately from each other instead of being mixed and water may be added to either or both of the two, or, alternatively, the radical polymerizable monomer, the acid-reactive glass and water are provided separately instead of being mixed, and thereafter each components are mixed just before an application, or one component is applied first onto a tooth and then others applied thereon successively, whereby embodying the present invention.

In a typical case, Liquid A containing water, an acid-reactive filler, a water-soluble organic solvent and a polymerization catalyst and Liquid B containing a radical polymerizable monomer having an acid group, a water-soluble organic solvent and a polymerization catalyst are provided. In such case, upon the addition of the acid-reactive filler to Liquid B, Liquid B undergoes an acid-base reaction between the acid-reactive filler and the polymerizable compound having an acid group due to the presence of a trace amount of water, resulting in a gradual increase in the viscosity. Accordingly, the acid-reactive filler should be separated from the monomer having an acid group and added to Liquid A, and this mode of the present invention is the most preferred in view of the shelf life of a dental adhesive of the present invention. When a composition of the present invention is used in this mode as a dental adhesive or a dental adhesive resin cement, it may be applied onto the surface of a tooth directly or after an acid etching treatment.

While the present invention is intended to be used mainly in the field of a dental surgery, it can also be used as an adhesive to a biological hard tissue in the fields of a surgery, an orthopedics and a plastic surgery.

The present invention is further described in detail in the following examples, which are not intended to restrict the invention.

EXAMPLES 1 TO 5 AND COMPARATIVE EXAMPLES 1 TO 8

Components (A) to (E) in the respective amounts shown in Table 1 were used to form various adhesive compositions (Examples 1 to 5 and Comparative Examples 1 to 8), each of which was used as a interface between a tooth and a composite resin, and evaluated for the adhesive strength, a sustained fluoride release level therefrom and the degrees of the water absorption and the swelling. Component (E) as a polymerization catalyst consisted of 1.5% by weight of sodium p-toluenesulfinate, 1.0% by weight of 1,3,5-trimethylbarbituric acid and 0.2% by weight of camphorquinone, based on the total amount of (A+B+C+D).

In Table 1, Components (A), (B), (C) and (D) represents a polymerizable unsaturated monomer, an acid-reactive filler, water and a water-soluble organic solvent, respectively.

The results of the adhesives tested are shown in Table 2.

The characteristics of an adhesive were evaluated as follows.

(1) Method of Adhesion Test

The shear bond strength between a photopolymerizable composite resin LITE-FIL IIA (available from K.K. SHOFU) and an enamel or a dentin using an adhesive prepared was measured. A tooth employed was a freshly extracted bovine anterior tooth instead of a human tooth, and was subjected to the test after removing the root of the tooth followed by embedding the tooth in an epoxy resin. In the bonding test, the labial surface of the bovine tooth was ground with a water-proof sandpaper to expose an enamel or a dentin, which was subjected to No. 600 grinding and then ruled for the adhesion area by applying a double-faced adhesive tape having a hole whose diameter was 4 mm, and then this area was coated with the adhesive shown in Table 1, which was allowed to stand for 30 seconds and then air-dried for 5 seconds gently with a compressed air. Subsequently, a visible light was irradiated for 30 seconds using SHOFU GLIP-LIGHT II (available from K.K. SHOFU.). After photocuring, a plastic mold having the inner diameter of 4 mm and the height of 2 mm was fixed, and packed with LITE-FIL IIA and then irradiated with a visible light for 30 seconds using SHOFU GLIP-LIGHT II (available from K.K. SHOFU). After photocuring, the mold was removed and the bonding test specimen was obtained. This bonding test specimen was immersed for 24 hours in distilled water at 37° C., and then the shear bond strength was measured using Instron type testing machine (Instron Model 5567) at the crosshead speed of 1 mm/min.

For a thermal cycling test, the bonding test specimen was immersed in a distilled water for 24 hours at 37° C., followed by 1 minutes at 4° C. followed by 1 minute at 60° C., which was repeated 5000 times. Thereafter, the bonding strength was measured as described above.

(2) Measurement of the Amount of Fluoride Release

A stainless steel ring whose inner and outer diameters are 15 mm and 20 mm, respectively, and whose height was 1 mm was mounted on a slide glass and then the hole was filled with a slightly excessive dental adhesive composition carefully to prevent the inclusion of air bubbles. A slide glass was fixed on a mold and irradiated for 30 seconds with the light source being in a close contact. This procedure was repeated for several times in order to ensure the irradiation over the entire sample. After allowing to stand at room temperature for 30 minutes, a sample which was 15 mm in diameter and 1 mm in thickness was taken out from the ring. After allowing to stand for 24 hours in a wet box at 37° C., the amount of fluoride ion released from the sample into 15 ml of the ion exchange water over 1 week at 37° C. was measured using a fluoride ion electrode F-125 (manufactured by TOA DENPA Co.), a reference electrode HS-305DP (manufactured by TOA DENPA Co.), an ion meter (TDA, pH meter) with 1 ml of TISAB 11 (ORION, USA) being added as an ion level adjusting agent per 10 ml of the sample solution. The amount of fluoride release per unit area was expressed in $\mu g/cm^2$.

(3) Measurement of the Amount of Water Absorption

A sample which was 15 mm in diameter and 1 mm in thickness was prepared similarly, and allowed to stand in a wet box at 37° C. for 24 hours, and then weighed for the initial weight. After immersing in 15 mL of water at 37° C. for 5 days, the sample was wiped with a tissue paper and weighed after 1 minute. The amount of water absorption per unit volume was expressed in $\mu g/mm^3$.

(4) Measurement of Swelling

A cylindrical sample which was 3 mm in diameter and 6 mm in height was prepared similarly, and allowed to stand in a wet box at 37° C. for 24 hours, and then examined for the vertical dimension ($L_0$). After immersing in 15 mL of water at 37° C. for 2 days, the sample was wiped with a tissue paper and examined for the vertical dimension (L). Based on the following equation, the change in the dimension was calculated as a % swelling.

% Swelling=$\{(L-L_0)/L_0\} \times 100$

TABLE 1

| | Component (A) (100 parts by weight) | | | Component (B) (by weight) | Component (C) (by weight) | Component (D) (by weight) |
|---|---|---|---|---|---|---|
| | 4-AET | 2-HEMA | UTA | FG | water | acetone |
| Example | | | | | | |
| 1 | 35 | 48 | 17 | 48 | 43 | 26 |
| 2 | 39 | 56 | 5 | 83 | 72 | 22 |
| 3 | 35 | 50 | 15 | 75 | 50 | 25 |
| 4 | 35 | 50 | 15 | 75 | 45 | 30 |
| 5 | 31 | 47 | 22 | 62 | 35 | 33 |
| Comparative Example | | | | | | |
| 1 | 29 | 54 | 17 | 39 | 4 | 36 |
| 2 | 29 | 54 | 17 | 39 | 0 | 39 |
| 3 | 27 | 69 | 4 | 59 | 8 | 29 |
| 4 | 25 | 64 | 11 | 55 | 0 | 27 |
| 5 | 25 | 37 | 38 | 25 | 8 | 33 |
| 6 | 30 | 44 | 26 | 25 | 5 | 37 |
| 7 | 25 | 36 | 39 | 25 | 0 | 39 |
| 8 | 35 | 50 | 15 | 10 | 45 | 30 |

(Abbreviation)
4-AET: 4-Acryloxyethyltrimellitic acid,
2-HEMA: 2-Hydroxyethyl methacrylate,
UTA: Urethane triacrylate,
1,1,1-Tri{6-[(1-acryloxy-3-phenoxy)-2-isopropoxycarbonylamino]-hexylcarbamoyloxymethyl}propane,
FG: Fluoroaluminosilicate glass

TABLE 2

| | Shear bond strength (MPa) | | Amount of fluoride release ($\mu g/cm^2$) | Amount of water absorption ($\mu g/mm^3$) | Swelling (%) |
|---|---|---|---|---|---|
| | Enamel | Dentin | | | |
| Example | | | | | |
| 1 | 19.4 | 16.5 | 32.30 | 30.6 | 0.82 |
| 2 | 14.6 | 13.9 | 37.61 | 40.6 | 0.06 |
| 3 | 18.3 | 14.4 | 17.00 | 39.6 | 0.07 |
| 4 | 14.4 | 13.9 | 10.15 | 56.1 | 0.09 |
| 5 | 19.5 | 18.6 | 8.00 | 85.9 | 0.84 |
| Comparative Example | | | | | |
| 1 | 9.8 | 10.1 | 13.69 | 227.6 | 3.51 |
| 2 | 9.5 | 13.0 | 13.38 | 257.6 | 4.66 |
| 3 | 7.6 | 10.6 | 8.00 | 180.5 | 3.15 |
| 4 | 9.0 | 9.4 | 9.75 | 261.3 | 4.07 |
| 5 | 9.6 | 10.2 | 11.43 | 183.4 | 3.91 |
| 6 | 5.0 | 9.8 | 13.40 | 182.3 | 5.12 |
| 7 | 8.0 | 5.9 | 13.94 | 254.8 | 5.40 |
| 8 | 7.1 | 6.6 | 5.23 | 268.5 | 6.24 |

The shear bond strength of the adhesive of Comparative Example 1 to 8 to an enamel and to a dentin ranged from 5.0 to 8 MPa and 5.9 to 13.0 MPa, respectively, while those of Examples 1 to 5, which were the inventive composition, to an enamel and to a dentin were as high as 14.4 to 19.5 MPa and 13.9 to 18.6 MPa, respectively. In addition, the amounts of the water absorption and the swelling of Comparative Examples 1 to 8 ranged from 180.5 to 268.5 $\mu g/mm^3$ and 3.15 to 6.24%, respectively, while those of Examples 1 to 5 were as extremely low as 30.6 to 85.9 $\mu g/mm^3$ and 0.07 to 0.84%, respectively. The amount of fluoride release of the inventive compositions tended to be higher.

EXAMPLE 6 AND COMPARATIVE EXAMPLES 9 TO 12

Using the dental adhesive compositions shown in Table 3, the shear bond strength of the adhesive to a tooth, the amount of fluoride release, the amount of water absorption and the swelling were measured using the same test method for Example 1. Component (E) as a polymerization catalyst consisted of 1.5% by weight of sodium p-toluenesulfinate, 1.0% by weight of 1,3,5-trimethylbarbituric acid and 0.2% by weight of camphorquinone, based on the entire composition.

Comparative Example 9 was similar to Example 6 except for containing no Component (C) which was water, and Comparative Example 10 was similar to Example 6 except that it did not contain Component (C) and Component (D). Comparative Example 11 was similar to Example 6 except for containing no Component (B), and Comparative Example 12 was also similar to Example 6 except for containing a silica filler instead of Component (B).

The results are shown in Table 4.

pulverized to the mean particle size of 5 μm. To 60.0 g of this glass suspended in 524 mL of deionized water, an aqueous solution of polyacrylic acid consisting of 96.0 g of an aqueous solution of polyacrylic acid (% solid: about 40% by weight, degree of polymerization: about 1100) and 238 mL of deionized water was added over 1 hour. Then the mixture was kept at 48 to 52° C. for 3.5 hours. This mixture was dried at 115° C. using a spray drier, and then further dried for 1 day using a freeze drier, whereby obtaining a preformed glass ionomer filler. Hereinafter, this is referred-to as a PRG filler. On the other hand, a resin composition was prepared by mixing 45% by weight of bisphenol A-diglycidyl methacrylate, 43% by weight of triethylene glycol dimethacrylate, 10% by weight of 2-hydroxyethyl methacrylate, 0.7% by weight of camphorquinone and 1.3% by weight of N,N-dimethylaminoethyl methacrylate. 33.0% by weight of the resin composition obtained and 67.0% of the PRG filler described above were mixed to obtain an experimental composite resin.

Method of Marginal Leakage Test

In the leakage test, a freshly extracted bovine anterior tooth was used and a full enamel margin cavity and a

TABLE 3

|  | Component (A) (100 parts by weight) | | | Component (B) (by weight) | Component (C) (by weight) | Component (D) (by weight) |
| --- | --- | --- | --- | --- | --- | --- |
|  | 4-AET | 2-HEMA | UTA | FG | water | acetone |
| Example 6 | 38 | 50 | 12 | 63 | 50 | 38 |
| Comparative Example 9 | 25 | 33 | 42 | 42 | 0 | 25 |
| Comparative Example 10 | 20 | 27 | 53 | 63 | 0 | 0 |
| Comparative Example 11 | 38 | 50 | 12 | 0 | 50 | 38 |
| Comparative Example 12 | 38 | 50 | 12 | 63* | 50 | 38 |

*Silica filler

TABLE 4

|  | Shear bond strength (0 cycle) (MPa) | | Shear bond strength after thermal cycled (MPa) | | The amount of fluoride release | The amount of water absorption | Swelling |
| --- | --- | --- | --- | --- | --- | --- | --- |
|  | Enamel | Dentin | Enamel | Dentin | (μg/cm$^2$) | (μg/mm$^3$) | (%) |
| Example 6 | 19.4 | 16.2 | 20.7 | 19.1 | 25.29 | 32.5 | 1.02 |
| Comparative Example 9 | 12.5 | 10.9 | 8.2 | 7.4 | 8.32 | 256.7 | 4.43 |
| Comparative Example 10 | 9.5 | 9.4 | 8.0 | 6.8 | 7.10 | 285.5 | 4.81 |
| Comparative Example 11 | 10.2 | 11.3 | 3.3 | 4.1 | None | 168.0 | 2.32 |
| Comparative Example 12 | 8.2 | 4.4 | 3.1 | 2.0 | None | —* | —* |

*did not test

The adhesive compositions described above were subjected also to a marginal leakage test by the method described below.

(5) Marginal Leakage Test

Preparation of Experimental Composite Resin 18.8% by weight of aluminum oxide, 34.4% by weight of silica, 22.4% by weight of calcium fluoride, 8.4% by weight of aluminum phosphate and 16.0% by weight of aluminum fluoride were fused together to form a glass, which was cervical cavity, as shown in FIG. 1, were prepared with running water using a spherical diamond point HP 42 (manufactured by K.K. SHOFU) (φ3.3 mm).

Figure 2:
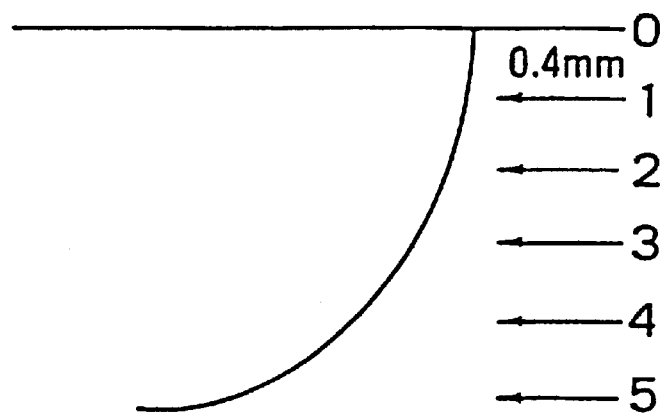
FIG. 2 shows the criteria based on which the marginal leakage was scored.

The procedure of adhesive restoration involved an application of each adhesive whose composition is shown in Table 3 to the entire cavity followed by an interval of 30 seconds prior to an air-drying for 5 seconds gently with a compressed air followed by an irradiation with a visible light for 20 seconds. After photocuring, the cavity was filled with the experimental composite resin described above and irradiated with a visible light for 30 seconds using SHOFU GLIP-LIGHT II. After photocuring, the marginal leakage test specimen was immersed in distilled water at 37° C. for 24 hours, and then the composite resin surface and the margin were polished successively with a WHITE POINT (manufactured by K.K. SHOFU) and a SUPERSNAP (manufactured by K.K. SHOFU). Subsequently, the specimen was subjected to a thermal cycle consisting of an immersion in water for 1 minutes at 4° C. followed by 1 minutes at 60° C., which was repeated 2000 times. Prior to this thermal cycle, the tip of the root of the tooth was enclosed with an self-curing acrylic resin. After the acrylic resin was cured, the specimen was immersed in a 0.5% basic fuchsine aqueous solution at 37° C. for 24 hours. After air-drying, the sample was sectioned along the center of the cavity using a diamond disk 62TD (manufactured by K.K. SHOFU). The sectional area was dry-ground with SiC 1200. The sectional area of the cavity was observed microscopically (×60) and the marginal leakage was scored based on the criteria shown in FIG. 2.

The results are shown in Table 5.

TABLE 5

|  | Full enamel margin cavity ① | | Full enamel margin Cavity ② | | Cervical cavity | |
| --- | --- | --- | --- | --- | --- | --- |
|  | Incisal | Cervical | Incisal | Cervical | Incisal | Root side |
| Example 6 | 0.8 | 0.8 | 1.0 | 0.2 | 0.7 | 0.5 |
| Comparative Example 9 | 1.3 | 2.0 | 1.2 | 1.3 | 2.0 | 0.2 |
| Comparative Example 10 | 0.8 | 1.0 | 2.0 | 1.3 | 0.7 | 1.0 |
| Comparative Example 11 | 2.0 | 1.7 | 2.0 | 1.7 | 3.0 | 1.8 |
| Comparative Example 12 | 1.7 | 1.7 | 2.0 | 2.0 | 3.0 | 1.7 |

Since in Comparative Example 9 an ion dissociation of a radical polymerizable monomer having an acid group, which should be effected by Component (C), i.e., water, was insufficient, the adhesiveness and the amount of fluoride release were poor and the amount of water absorption and the swelling were increased. Comparative Example 10 was similar to Comparative Example 9. Similar tendency was noted also in the marginal leakage test. The results of the marginal leakage test also proved that the dental adhesive compositions of the present invention were excellent.

Comparative Example 11, a composition which contained no acid-reactive filler, exhibited a low figure of the shear bond strength to both of the enamel and the dentin. Also, it was observed that some specimens underwent a fall-down of the composite particularly after the thermal cycled, thus showing an extremely poor adhesive durability. Comparative Example 12, a composition which contained a silica filler instead of an acid-reactive filler, it showed a poor adhesive durability after the thermal cycled, which leaded to a high score in the marginal leakage test, with some fall-downs being noted. Comparative Examples 11 and 12 exhibited no sustained release of fluoride ion from the cured adhesives.

When the amount of water absorption and the swelling were compared between Example 6 and Comparative Examples 9 to 12, those in Comparative Examples 9 to 12 were 168.0 to 285.5 $\mu g/mm^3$ and 2.32 to 4.81%, respectively, but those of the inventive composition in Example 6 were as low as 32.5 $\mu g/mm^3$ and 1.02%, respectively, which corresponded to the reductions to 1/5 to 1/9 and 1/2 to 1/5, respectively.

EXAMPLES 7 TO 10

Adhesive compositions were prepared similarly to Example 1 except for using a compound shown in Table 6 instead of 4-AET as a radical polymerizable monomer having an acid group (Component A), and examined for the shear bond strength, the amount of fluoride release, the amount of water absorption and the swelling. The results are shown in Table 6.

TABLE 6

| Example | Component (A) parts by weight | Shear bond strength (MPa) | | The amount of fluoride release ($\mu g/cm^2$) | The amount of water absorption ($\mu g/mm^3$) | Swelling (%) |
| --- | --- | --- | --- | --- | --- | --- |
| | | Enamel | Dentin | | | |
| Example 7 | 6-MHPA | 18.4 | 16.4 | 42.37 | 26.97 | 0.97 |
| Example 8 | 6-MHPP | 14.5 | 15.9 | 53.76 | 32.72 | 0.68 |
| Example 9 | 4-MET | 17.6 | 17.4 | 24.50 | 24.06 | 1.20 |
| Example 10 | 4-AETA | 19.9 | 18.0 | 19.93 | 38.61 | 0.88 |

(Abbreviation)
6-MHPA: (6-Methacryloxy)hexylphosphonoacetate,
6-MHPP: (6-Methacryloxy)hexyl-3-phosphonopropionate,
4-MET: 4-Methacryloxyethyltrimellitic acid,
4-AETA: 4-Acryloxyethyltrimellitate anhydride, Examples 7 to 10 were excellent in terms of all of the shear bond strengths, the amount of fluoride release, the amount of water absorption and the swelling.

EXAMPLE 11

An adhesive composition consisting of 100 parts by weight of a polymerizable unsaturated monomer (Component A) consisting of 38% by weight of 4-AET, 50% by weight of 2-HEMA and 12% by weight of UTA, 62 parts by weight of FG (Component B), 1 part by weight of a PRG filler, 50 parts by weight of water (Component C) and 38 parts by weight of acetone (Component D) was prepared.

Based on the entire composition, 1.5% by weight of sodium p-toluenesulfinate, 1.0% by weight of 1,3,5-trimethylbarbituric acid and 0.2% by weight of camphorquinone were added as a polymerization catalyst (Component (E)). The shear bond strength to a tooth, the amount of fluoride release, the amount of water absorption and the swelling for the adhesive composition described above were measured by the methods similar to those in Example 1. This composition exhibited the shear bond strengths to the enamel and the dentin which were as high as 17.8 MPa and 15.5 MPa, respectively, and was excellent also in the terms of the sustained fluorine release level, the water absorption and the swelling, which were 21.51 $\mu g/cm^2$, 31.5 $\mu g/mm^3$ and 0.88%, respectively.

EXAMPLE 12

An adhesive composition consisting of 100 parts by weight of a polymerizable unsaturated monomer (Component A) consisting of 38% by weight of 4-AET, 50% by weight of 2-HEMA and 12% by weight of UTA, 58 parts by weight of FG (Component B), 5 parts by weight of a PRG filler, 50 parts by weight of water (Component C) and 38 parts by weight of acetone (Component D) was prepared. Based on the entire composition, 1.5% by weight of sodium p-toluenesulfinate, 1.0% by weight of 1,3,5-trimethylbarbituric acid and 0.2% by weight of camphorquinone were added as a polymerization catalyst (Component (E)). This composition was examined for the shear bond strength to a tooth, the amount of fluoride release, the amount of water absorption and the swelling by the methods similar to those in Example 1. This composition exhibited the shear bond strengths to the enamel and the dentin which were as high as 18.2 MPa and 15.8 MPa, respectively, and was excellent also in the terms of the amount of fluoride release, the amount of water absorption and the swelling, which were 35.02 $\mu g/cm^2$, 33.8 $\mu g/mm^3$ and 0.95%, respectively.

TABLE 7

| | Number of steps in adhesion procedure | Adherent to be adhered | Shear bond strength (MPa) | | |
|---|---|---|---|---|---|
| | | | After 24 hours | 2000 cycles | 10000 cycles |
| Example 11 | 1 | Enamel | 17.8 | 17.3 | 21.6 |
| | | Dentin | 15.5 | 15.0 | 15.9 |
| Reference Example Fluorobond | 2 | Enamel | 19.3 | 20.3 | 17.7 |
| | | Dentin | 22.2 | 18.1 | 20.4 |

Table 7 shows the durability of the adhesion of Example 11 and Fluorobond (available from K.K. SHOFU) to the enamel and the dentin. The method of the adhesion was similar to those in Example 1. Fluorobond was a 2-step adhesive system consisting of a primer and a bonding agent, and contained no FG (Component B) which was a component of the present invention. In spite of a simple 1-step procedure of Example 11 of the invention, the adhesion durability overcoming the 10000 thermal cycles comparable to 2-step Fluorobond, thus proving an advanced technology of the invention.

EXAMPLE 13

An adhesive composition was prepared similarly to Example 6 except for using 2-hydroxy-3-(3,4-dimethyl-9H-thioxanthen-2-yloxy)N,N,N-trimethyl-1-propanaminium chloride instead of camphorquinone in the polymerization catalyst Component (E). This composition was examined for the shear bond strength to a tooth, the amount of fluoride release, the amount of water absorption and the swelling by the methods similar to those in Example 1 except for using an experimental composite resin instead of LITE-FIL II. This composition exhibited the shear bond strengths to the enamel and the dentin which were as high as 15.1 MPa and 19.6 MPa, respectively, and was excellent also in the terms of the amount of fluoride release, the amount of water absorption and the swelling, which were 33.68 $\mu g/cm^2$, 30.6 $\mu g/mm^3$ and 0.83%, respectively.

EXAMPLE 14

An adhesive composition was prepared similarly to Example 6 except for replacing a half of camphorquinone in the polymerization catalyst Component (E) with 2-hydroxy-3-(3,4-dimethyl-9H-thioxanthen-2-yloxy)N,N,N-trimethyl-1-propanaminium chloride. This composition was examined for the shear bond strength to a tooth, the amount of fluoride release, the amount of water absorption and the swelling by the methods similar to those in Example 1 except for using an experimental composite resin instead of LITE-FIL II. This composition exhibited the shear bond strengths to the enamel and the dentin which were as high as 14.3 MPa and 16.1 MPa, respectively, and was excellent also in the terms of the amount of fluoride release, the amount of water absorption and the swelling, which were 35.62 $\mu g/cm^2$, 29.8 $\mu g/mm^3$ and 0.91%, respectively.

EXAMPLE 15

An adhesive composition consisting of 100 Parts by weight of a polymerizable unsaturated monomer (Component A) consisting of 41% by weight of 4-AET, 53% by weight of 2-HEMA and 6% by weight of UTA, 65 parts by weight of FG (Component B), 1 part by weight of a PRG filler, 53 parts by weight of water (Component C) and 40 parts by weight of acetone (Component D) was prepared. Based on the entire composition, 1.5% by weight of sodium p-toluenesulfinate, 1.0% by weight of 1,3,5-trimethylbarbituric acid and 0.2% by weight of camphorquinone were added as a polymerization catalyst (Component (E)).

Figure 3:
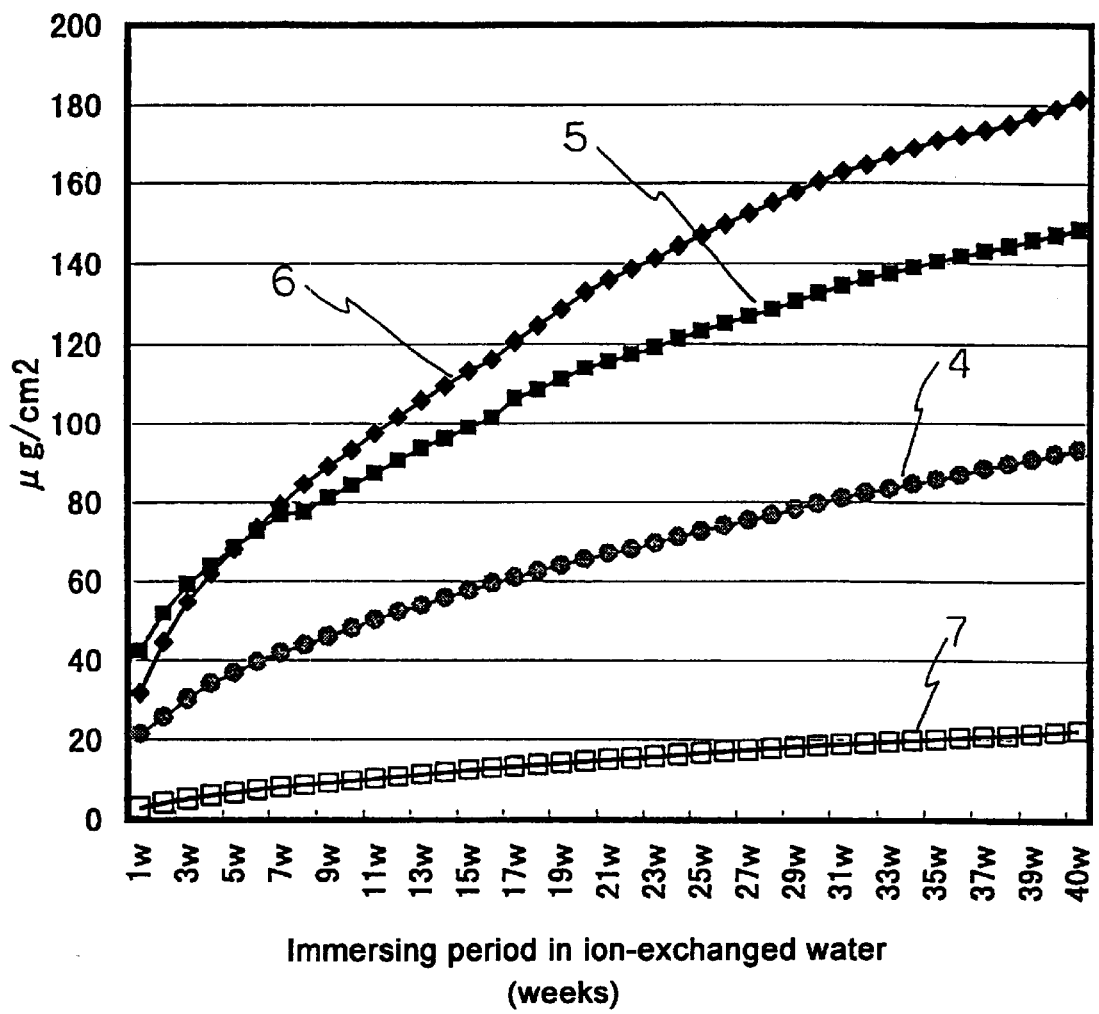
FIG. 3 shows a cumulative fluoride release.

FIG. 3 shows a cumulative fluoride release of Example 11, Example 15, Fluorobond and glass ionomer CX. Example 11 and 15 have more excellent stained fluoride release function in comparison with Fluorobond which does not contain acid-reactive filler as component B of the present invention. On the other hand, dental glass ionomer has been evaluated in the availability to surgery such as effectiveness of secondary caries inhibition by its high sustained fluoride release property. The adhesive composition of the present invention has a high sustained fluoride release function comparable with glass ionomer CX which is a dental glass ionomer cement.

A dental adhesive composition of the invention enables an excellent adhesion to a substrate such as an enamel and a dentin of a tooth only by a simple one-step procedure and has a marked sustained fluoride-releasing function to strengthen a tooth substrate, and thus is expected to inhibit the formation of a secondary caries. While this invention is intended to be used mainly in the field of a dental surgery, it can also be used as an adhesive to a biological hard tissue in the fields of a surgery, an orthopedics and a plastic surgery.

What is claimed is:

1. A dental adhesive composition comprising:
   a first liquid component, said first liquid component comprising:
   (A) 100 parts by weight of a polymerizable unsaturated monomer containing 5% by weight or more of a radical polymerizable monomer having an acid group, and
   (E) 1 to 10 parts by weight of a polymerization catalyst;
   a second liquid component comprising:
   (C) 35 to 100 parts by weight of water, and
   (D) 5 to 100 parts by weight of water-soluble organic solvent; and
   (B) 0.1 to 10 parts by weight of a polymerization catalyst,
   wherein the first liquid component and the second liquid component are maintained separately until use.

2. A method of bonding dental components comprising:
   mixing the first liquid component and second liquid component of claim 1 to provide a dental adhesive, and immediately thereafter, applying the dental adhesive to a dental component.

3. A dental adhesive composition according to claim 1 wherein the acid group of said radical polymerizable monomer having an acid group is selected from the group consisting of carboxyl group and an acid anhydride residue thereof and phosphate group.

4. A dental adhesive composition according to claim 1 wherein said acid-reactive filler is a fluoroalumnosilicate glass.

5. A dental adhesive composition according to claim 1 wherein said water-soluble organic solvent is selected from the group consisting of acetone, ethyl alcohol and isopropyl alcohol.

6. A dental adhesive composition according to claim 1 wherein said polymerization catalyst is at least one selected from the group consisting of a barbituric acid derivative, an organic peroxide, an α-diktone, an amine, a sulfinic acid, and an organotin compound.

7. A dental adhesive composition according to claim 1 wherein said radical polymerizable monomer having an acid group is at least one selected from the group consisting of 4-(meth)acryloxyethyltrimellitic acid, 4-(meth)acryloxyethyltrimellitate anhydride, (6-(meth)acryloxy)hexyl-3-phosphonopropionate and (6-(meth)acryloxy)hexyl-3-phosphonoacetate.

8. A dental adhesive composition according to claim 1 wherein said radical polymerizable monomer having an acid group is at least one selected from the group consisting of 4-(meth)acryloxyethyltrimellitic acid, 4-(meth)acryloxyethyltrimellitate anhydride, (6-(meth)acryloxy)hexyl-3-phosphonopropionate and (6-(meth)acryloxy)hexyl-3-phosphonoacetate.

9. A dental adhesive composition according to claim 3, wherein said polymerization catalyst is at least one selected from the group consisting of 1-benzyl-5-phenylbarbituric acid, 1-cyclohexyl-5-ethylbarbituric acid, 5-butylbarbituric acid, 1,3,5-trimethylbarbituric acid, benzoyl peroxide, t-butyl peroxymaleic acid, succinic acid peroxide, camphor quinone, sodium benzenesulfinate, sodium p-toluenesulfinate, di-n-butyltin dimalate, di-n-octyltin dimalate, di-n-octyltin dilaurate, di-n-butyltin dilaurate, and 2-hydroxy-3-(3,4-dimethyl-9H-thioxanthen-2-yloxy)N,N,N-trimethyl-1-propanaminium chloride.

10. A dental adhesive according to claim 1, further comprising at least one of a preformed glass ionomer filler and a colloidal silica other than an acid-reactive filler.

11. A dental adhesive composition according to claim 1, wherein said acid-reactive filler contains fluorine.

12. A dental adhesive composition according to claim 3 wherein said water-soluble organic solvent is selected from the group consisting of acetone, ethyl alcohol and isopropyl alcohol.

13. A dental adhesive composition according to claim 3 wherein said polymerization catalyst is at least one selected from the group consisting of a barbituric acid derivative, an organic peroxide, an α-diketone, an amine, a sulfinic acid, and an organotin compound.

14. A dental composition according to claim 13, exhibiting a sustained release of fluorine.

15. A dental adhesive composition according to claim 4, exhibiting a sustained release of fluorine.

16. A dental adhesive composition according to claim 3 wherein said polymerization catalyst is at least one selected from the group consisting of 1-benzyl-5-phenylbarbituric acid, 1-cyclohexyl-5-ethylbarbituric acid, 5-butylbarbituric acid, 1,3,5-trimethylbarbituric acid, benzoyl peroxide, t-butyl peroxymaleic acid, succinic acid peroxide, camphor quinone, sodium benzenesulfinate, sodium p-toluenesulfinate, di-n-butyltin dimalate, di-n-octyltin dimalate, di-n-octyltin dilaurate, di-n-butyltin dilaurate, and 2-hydroxy-3(3,4-dimethyl-9H-thioxanthen-2-yloxy)N,N,N-trimethyl-1-propanaminium chloride.

17. A dental adhesive composition according to claim 1, wherein said acid-reactive filler contains fluorine.

18. A dental adhesive composition according to claim 4 further comprising at least one of a preformed glass ionomer filler and a colloidal silica other than a fluoroaluminosilicate glass.

19. A dental adhesive composition according to claim 1 comprising a fluorine containing compound.

20. A dental composition according to claim 17, exhibiting a sustained release of fluorine.

21. A dental adhesive composition according to claim 4, exhibiting a sustained release of fluorine.

22. A dental adhesive composition according to claim 17, exhibiting a sustained release of fluorine.

23. A dental adhesive composition according to claim 1, wherein said radical polymerizable monomer comprises one or more selected from the group consisting of 4-(meth)acryloxyethyltrimellitic acid, 4-metacryloxyethyltrimellitic acid, 4-(meth)-acryloxyethyltrimellitate anhydride, 11-(meth)acryloxy-1,1-undecane dicarboxylic acid, 2-(meth)acryloxyethylphosphate, bis[2-(meth)acryloxyethyl]phosphate, 2-(meth)acryloxyethyl phenyl hydrogen phosphate, 10-(meth)acryloxydecyl dihydrogen phosphate, vinylphosphonic acid, p-vinylbenzylphosphonic acid, (2-(meth)acryloxy)ethyl-3-phosphonopropionate, (6-(meth)acruloxy)hexyl-3-phosphonoacetate, (10-(meth)acryloxy)decyl-3-phosponopropionate, N-(meth)acryloylaniline, N-(meth)acryloyltyrosine, N-(meth)acryloylaspartic acid, N-phenylglycidyl(meth)acrylate, P-vinybenzoic acid, N-(meth)acryloylaminobenzoic acid, and N-(meth)acryloylaminosalicylic acid.

24. A dental adhesive composition according to claim 1, wherein said acid-reactive filler is highly transparent glass produced by a method selected from the group consisting of a fusing method and a sol-gel method.

25. A method of bonding dental components comprising applying the dental adhesive composition of claim 1 to at least one dental component.

26. A method of bonding dental components comprising:
   providing the dental adhesive composition of claim 1;
   mixing the first liquid and the second liquid, and immediately thereafter, applying the mixture to a dental component.

27. A dental adhesive composition of claim 1, wherein the first liquid comprises to 100% by weight component (D) and the second liquid comprises 0 to 100% component (E).

* * * * *